United States Patent [19]

Cocito

[11] Patent Number: 4,991,791
[45] Date of Patent: Feb. 12, 1991

[54] EXPANSIBLE REEL FOR TESTS ON FILAMENTARY MATERIAL IN PARTICULAR OPTICAL FIBRES

[75] Inventor: Giuseppe Cocito, S. Giusto Can.Se, Italy

[73] Assignee: Sip- Societa Italiana Per L'Esercizio Delle Telecomunicazioni P.A., Turin, Italy

[21] Appl. No.: 431,377

[22] Filed: Nov. 2, 1989

[30] Foreign Application Priority Data

Nov. 16, 1988 [IT] Italy .................................. 68018 A/88

[51] Int. Cl.⁵ .............................................. B65H 75/24
[52] U.S. Cl. ................................. 242/110; 242/72 R; 242/72 B; 242/110.1
[58] Field of Search .................. 242/110, 110.1, 110.2, 242/110.3, 63, 72 R, 72 B; 73/793, 826, 829

[56] References Cited

U.S. PATENT DOCUMENTS

| | | | |
|---|---|---|---|
| 2,950,071 | 8/1960 | Tidland | 242/110.1 X |
| 3,047,250 | 6/1962 | Saether | 242/110.1 |
| 3,289,966 | 12/1966 | Richel | 242/110.1 X |
| 4,445,649 | 5/1984 | Yataki | 242/110 X |

FOREIGN PATENT DOCUMENTS 16629 of 1910 United Kingdom ............ 242/110.1

Primary Examiner—William A. Cuchlinski, Jr.
Assistant Examiner—Joseph A. Rhoa
Attorney, Agent, or Firm—Herbert Dubno

[57] ABSTRACT

An expansible reel is provided having a plurality of rigid structural members parallel to each other and to a central axis of the reel, joined at the ends to supports allowing small radial displacements of the members. Between contiguous rigid members there are placed inflatable members into which compressed air is introduced to space apart the rigid members when an optical fibre wound around the reel is to be submitted to tests under controlled tensile stress conditions.

12 Claims, 3 Drawing Sheets

EXPANSIBLE REEL FOR TESTS ON FILAMENTARY MATERIAL IN PARTICULAR OPTICAL FIBRES

FIELD OF THE INVENTION

The present invention relates to supports for filamentary material, and more particularly to an expansible reel for winding up the material and subjecting same to measurements and tests. Preferably the filamentary material is an optical fibre.

THE RELATED ART

When manufacturing optical fibres, it is necessary or desirable, after fibre drawing, to perform tests and measurements on the fibre itself. Typical of such tests are those measuring behavior under tensile-stress conditions and those measuring microbending losses. It is desirable to effect the measurements without removing the fibre from the support on which it has been wound, and hence, if the tests require subjecting the fibre to tensile stresses, the support is to be expansible.

A number of expansible and/or collapsible reels used to support skeins of textile yarns are already known. These known reels are, however, only designed to allow an easy removal of skeins formed on the reel, or an easy insertion and removal of same to transfer them from one place to another. There is no provision which allows execution of tests where a carefully controlled and uniform tensile stress is to be applied to the wire. A number of examples are described in Austrian Patent No. 127,367, German Patent No. 910,271 and U.S. Pat. Nos. 3,139,242 and 3,166,335.

A drum for winding up material which is being drawn is also known from European Patent No. 125,609. The drum comprises a cylindrical envelope made of a single piece of an airtight material with a certain degree of resiliency, around which the fibre is wound. The envelope delimits a chamber where the pressure can be varied to allow tests under controlled tensile stress conditions to be made on the fibre. The envelope base must be thicker than the side surface to ensure the envelope indeformability necessary to obtain uniform tensile stresses, which makes the drum difficult to manufacture.

SUMMARY OF THE INVENTION

The invention overcomes the aforementioned problems by providing an expansible reel which is simple to manufacture and allows execution of a wide range of tests.

The reel of the invention comprises a plurality of rigid elongated members, parallel to each other and to a central axis of the reel and joined at the ends to common supports so as to be radially displaceable with respect to such supports, as well as inflatable members, which are arranged between confronting side faces of said elongated elements, extend along substantially the whole length of the rigid members and are associated with means for connection to a system supplying gas under pressure to vary their internal pressure in a controlled manner, said rigid elongated members being substantially in contact with each other when no gas under pressure is introduced into the inflatable members and being progressively spaced apart from each other by said inflatable elements because of the introduction of gas inside the latter in order to submit the material wound on the reel to controlled stresses.

BRIEF DESCRIPTION OF THE INVENTION

The invention will become more apparent with reference to the annexed drawings, in which.

DETAILED DESCRIPTION

Figure 1:
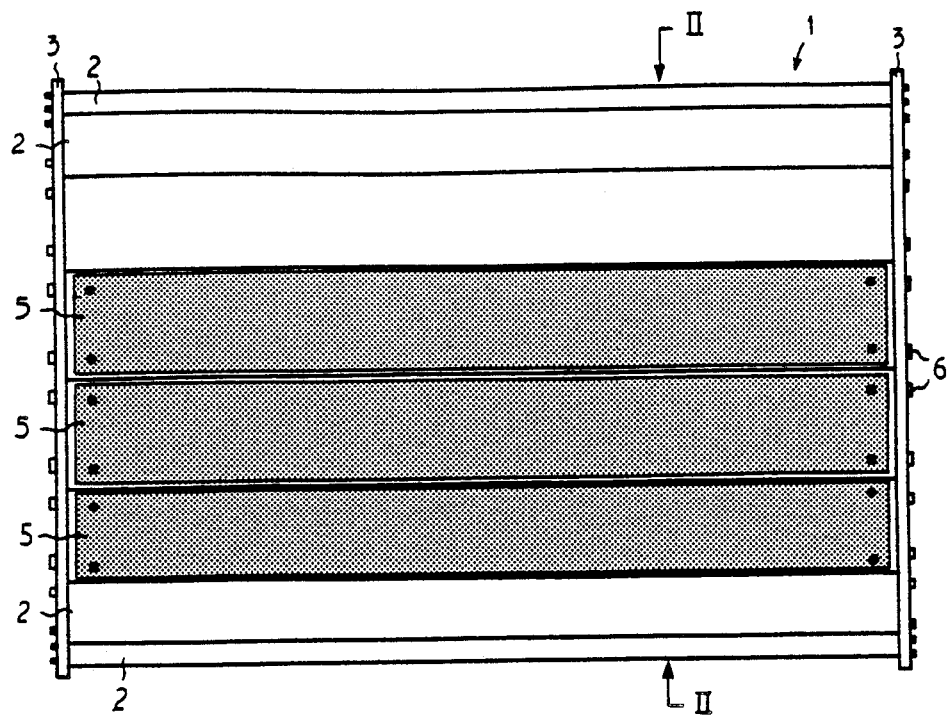
FIG. 1 is a side view of the reel according to the invention.
Figure 2:
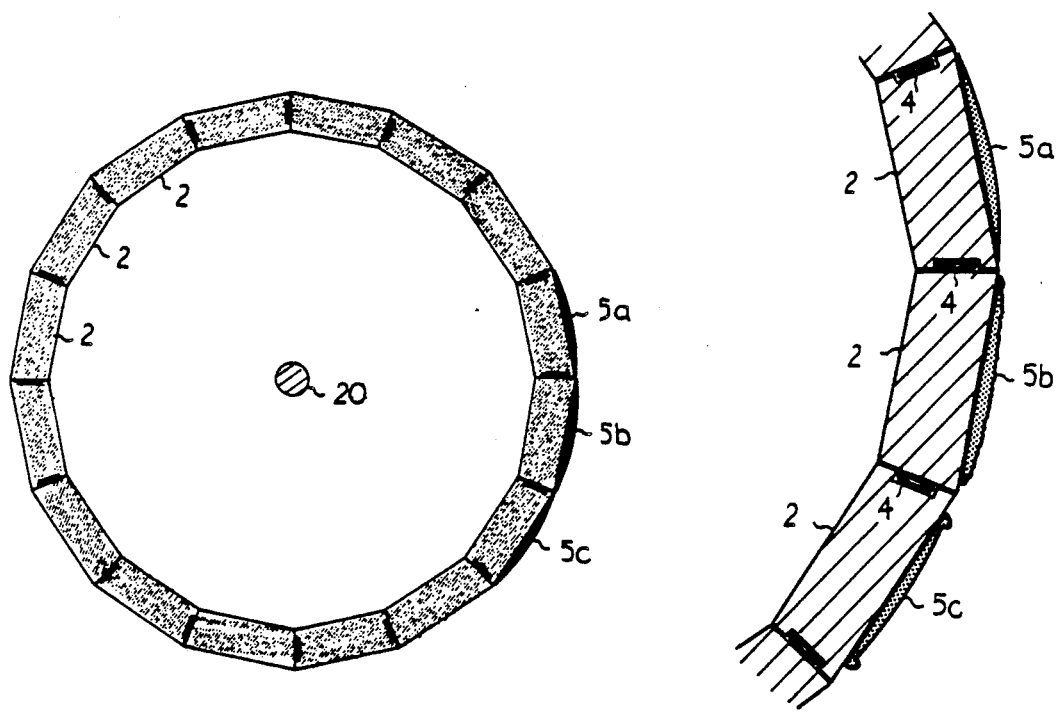
FIG. 2 is a cross-sectional view according to plane II—II of FIG. 1.
Figure 3:
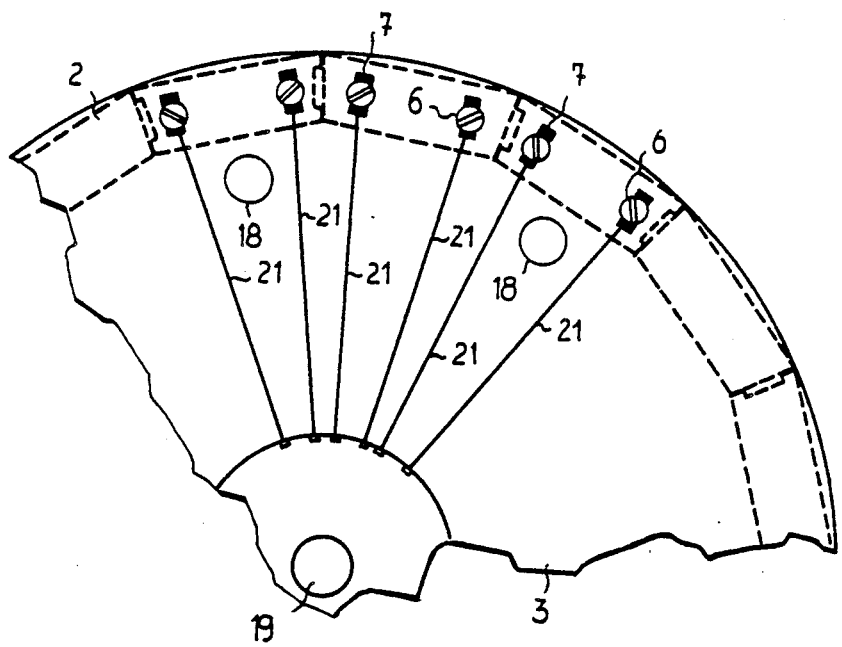
FIG. 3 is a partial view of a supporting disc.

As shown in FIGS. 1 to 3, the reel 1 according to the invention comprises a plurality of elongated structural elements 2 (hereinafter referred to as rods), which are made for instance of light metal, have a substantially trapezoidal section, are arranged parallel to each other around a central axis of the reel and are fastened at their ends to two discs 3.

Inflatable members 4 are positioned between contiguous rods, extending along substantially the whole rod length and are connectable to a compressed air source (not shown), placed outside the reel. To this aim one of the two discs 3 is provided with openings 18 where pipes can be connected with the compressed air source, which pipes communicate with the inside of the inflatable members as will be explained hereinafter. Members 4 can be tubular rubber members and, for the aims of the invention, must reach a diameter of several millimeters under conditions of maximum inflation. The contiguous rods are basically in contact with each other when no air is introduced into members 4 and will become more or less spaced apart upon introduction of compressed air into members 4.

Preferably, only every second rod is equipped with the inflatable members, which are associated with both side faces of the rod. However inflatable members 4 may also be associated with only one side surface of all rods 2.

Pads 5 with suitable shape and made of suitable material, for instance polyvinylchlòride or another hard plastic, tetrafluoroethylene, metal and the like, are fastened to the outer surface of rod 2. The shape and/or the material of the pads can be different depending on the tests to be made. For instance, if only tensile stress tests are to be made, pads with convex and smooth tensile stress tests are to be made, pads with convex and smooth surface can be used such as the pad denoted by 5a in FIG. 2, which extends over the whole width of the side surface of the corresponding rod and gives the reel a cylindrical surface basically without sharp corners.

To measure microbending losses, the surface of the pads can present a certain roughness, as shown for pad 5b; said roughness can be obtained by applying a coating of emery cloth or paper on pads like pads 5a or by making the whole pad of a material whose surface can be conveniently machined. If the fibre is to be subjected to higher strains, as demanded e.g. for adhesion tests of the primary coating, pads with an irregular surface like pad 5c could be used, which pad has a smaller width than the rod and presents two longitudinal ribs at the edges. The pads can be fastened to the rods in any suitable way, for instance by screws.

Figure 4:
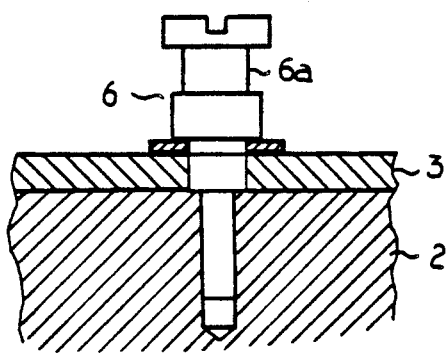
FIG. 4 shows a detail of the fastening of the reel elements to a supporting disc.

Rods 2 ought to be connected to discs 3 so as to allow small radial displacements (several millimeters) of the rods during the reel expansion, and to this aim discs 3 present slots where the head of a screw 6 or the like is fitted. For instance, as shown in FIG. 4, screws 6 acting as spacers can be used. These screws have a portion protruding outside discs 3 where a groove is realized which can be engaged by an end of a resilient member 21 (FIG. 3), for instance a spring, whose other end is gripped by pins or the like protruding from the discs. Unwanted movements of rods 2 are thereby avoided.

Discs 3 have a central recess 19 (FIG. 3) allowing the reel to be coupled to mechanisms rotating the reel for winding up the fibres. Additionally two of the discs 3 are linked by a rigid axial member 20 (FIG. 2), e.g. a tube, which prevents deformations of reel 1 which would be otherwise possible owing to loose connection among the rods 2 and the discs.

Figure 5:
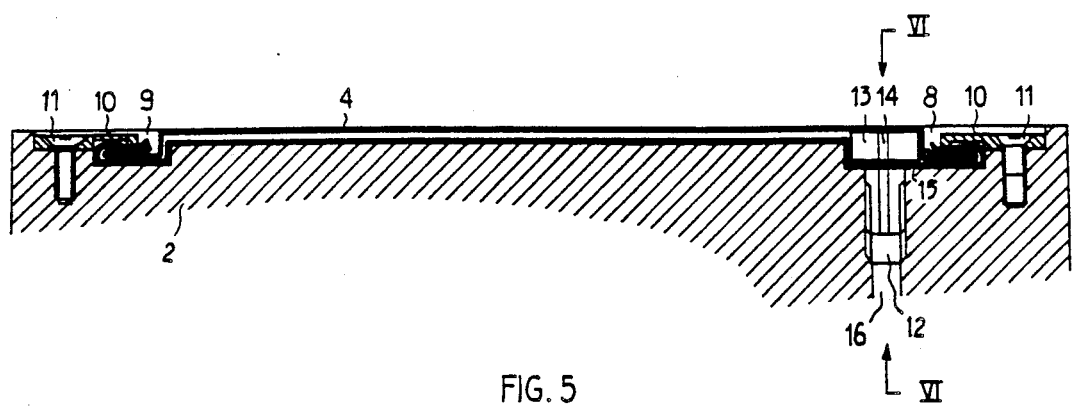
FIG. 5 is a longitudinal sectional view of a rod and of an associated inflatable member.
Figure 6:
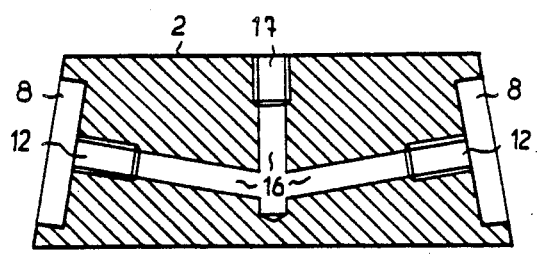
FIG. 6 is a cross sectional view of same, according to plane VI—VI of FIG. 5.

With reference to FIGS. 5 and 6, which relate to the case in which the inflatable members are associated with every second rod, the side faces of rods 2 present at the ends two recesses 8, 9 of different width wherein the end portions of the inflatable members 4 are held and closed. To this aim, the end portions of the inflatable members are folded onto themselves and the folded portions are pressed against the bottom of recesses 8, 9 by metal tangs secured e.g. by screws 11.

The wider recess 8 provides, moreover, a seat for a screw rivet 13 whose head is introduced into the inflatable member 4. Rivet 13 presents an axial through-hole and is associated with a washer 15 which keeps the tube wall compressed against the bottom of the recess. Seats 12 form the end portion of ducts 16 provided inside the rod 2 and communicating on one side with the interior of inflatable member 4, through the axial bore of rivet 13, and on the other side with a duct 17 which ends on the internal surface of rod 2. Duct 17 is connected, through suitable connectors, to the corresponding opening 18 (FIG. 3) on disc 3.

Where all rods 2 are equipped with an inflatable member 4, recesses 8, 9 will be provided on a single side face of the rods and a single duct 16 will be present ending on the inside rod surface.

The way of using the reel according to the invention is as follows. Before and during fibre winding, members 4 are kept deflated and rods 2 are kept blocked and basically in contact with each other by the springs engaging grooves 6a of screws 6. The fibre winding is performed with the usual techniques, so as to avoid overlapping of contiguous loops. The tensile stress applied to the fibre wound up in these conditions is practically null.

To carry out the measurements, air pressure is introduced into members 4, which are inflated and shift rods 2 outwards, thereby causing an increase in the reel diameter. Concomitantly the wound fib undergoes a certain strain, which depends on the pressure within the inflatable members. For example, the pressure applied to the inflatable members could range from 0 to 5 Atm. The system supplying the compressed air comprises adjustment valves and control instruments allowing the introduction of strictly controlled pressure variations. During the tests, resilient members 21 can be removed or kept in place, according to the type of tests.

Physical properties that may be measured by this arrangement include tensile stress, microbending loss adherence of the first coating or any other measurement wherein the fibre is to undergo a tensile stress. Depending on the tests to be performed, the most suitable pads 5 are mounted onto the rods prior to the winding. In addition, the fibre can be covered by a band wound on the reel, of which the surface in contact with the fibre presents a sinuous trend, for instance complementary to that given by pads 5c to the external surface of reel 1, or presents a desired roughness spectrum.

The reel with the wound fibre can be used to make measurements both in open air and with the fibre immersed in a liquid, e.g. water, at ambient temperature or at different temperatures. Measurements could also be taken inside furnaces, autoclaves, etc. These types of tests require the use of appropriate materials for rods 2.

If the fibre is wound on the reel while members 4 are slightly inflated, deflation thereof makes it possible to transfer the fibre as a skein to a convenient container. In this case the diameter of discs 3 should not exceed the diameter of the reel under rest conditions.

What has been described has been given only by way of non limiting example. Variations and modifications are possible without going beyond the scope of the invention as defined in the following claims. More particularly, even though reference was mainly made to optical fibres, the invention can be used to make tests on wires of whatever material, wherein behaviour under controlled tensile stress condition can be investigated.

I claim:

1. An expansible reel for winding filamentary material and for conducting tests and measurements on same, comprising:

a plurality of rigid elongated members each having first and second ends opposite another and a pair of side surfaces each extending between said first and second ends, said rigid elongated members oriented parallel to a central axis of said reel;

a pair of supports encompassing therebetween said rigid elongated members;

a plurality of fastening means for fastening said first and second ends of said rigid elongated members to a respective one of said supports, said fastening means allowing radial displacement of said rigid elongated members with respect to said supports;

a plurality of inflatable members positioned between confronting side surfaces of adjacent rigid elongated members, said inflatable members extending substantially over whole length of said side surfaces;

a plurality of means for connecting said inflatable members to a system supplying gas under pressure and capable of varying in a controlled manner an internal pressure of said inflatable members; and said rigid elongated members being substantially in contact with one another when gas under pressure is absent from said inflatable members but being progressively spaced from one another as gas is introduced into said inflatable members.

2. A reel according to claim 1, further comprising a tongue fastened to one of said side surfaces, said inflatable members being tubular and closed at ends thereof, said ends of said tubular inflatable members being compressed against said one of said side surfaces of said rigid elongated member.

3. A reel according to claim 1, further comprising a plurality of pads, at least one of said pads being supported against a respective outer surface of each of said rigid elongated members and said pads forming a pad surface onto which said filamentary material can be wound, said pads being interchangeable with other similar pads differing only in physical characteristics of said pad surface.

4. A reel according to claim 3, wherein said pads have a smooth and rounded external surface, each pad having a width basically equal to a width of said respective rigid elongated member.

5. A reel according to claim 3, wherein said pads each have a pad surface machined so as to present a predetermined roughness spectrum.

6. A reel according to claim 3, wherein said pads each have said pad surfaces covered with a material having a predetermined roughness spectrum.

7. A reel according to claim 3, wherein said pads each have a pad surface machined so as to present successions of recesses and protrusions with variable bonding radius.

8. A reel according to claim 1, wherein said means for connecting said inflatable members to a system supplying gas under pressure comprises a screw rivet which is located within a respective inflatable member and engages a seat provided in an end portion of said side surface of one of said rigid elongated members and forming and end portion of a duct formed within said end portion, said rivet presenting an axial through-hole communicating at one end with said inflatable member and at an other end with said seat.

9. A reel according to claim 8, wherein said means for connecting said inflatable members to said system supplying gas under pressure comprises a common duct communicating with said duct of said end portion of said rigid elongated member, said common duct extending through to said side surface of said rigid elongated member and connecting with an aperture on one of said supports, said aperture leading to a compressed gas supply.

10. A reel according to claim 1, further comprising a duct communicating with an inside of a respective inflatable member, said duct extending to one of said side surfaces of said rigid elongated members and connecting to an aperture formed in one of said supports, said aperture being connectable to a compressed gas supply, and each of said inflatable members being positioned on one of said side surfaces of each rigid elongated member.

11. A reel according to claim 1, further comprising a slot in each of said supports wherethrough pass said fastening means, said fastening means including a part protruding outward from said support and a groove within said protruding part, said groove serving as an engagement area for an end of a resilient member, said resilient member connecting one of said ends of said rigid elongated members to a central zone of one of said supports.

12. A reel according to claim 1, wherein said filamentary material is an optical fiber.

* * * * *